(12) United States Patent
Masaki et al.

(10) Patent No.: US 7,476,660 B2
(45) Date of Patent: Jan. 13, 2009

(54) COMPOSITION AND METHOD FOR ORGAN PRESERVATION

(75) Inventors: Yoshihiko Masaki, Kanagawa-Ken (JP); Kazunari Yoshida, Kanagawa-Ken (JP); Tadao Endo, Kanagawa-Ken (JP); Hirofumi Nakamura, Saitama-Ken (JP); Yasuhito Tashiro, Kanagawa-Ken (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 16 days.

(21) Appl. No.: 10/508,779

(22) PCT Filed: Mar. 28, 2003

(86) PCT No.: PCT/JP03/04024

§ 371 (c)(1),
(2), (4) Date: Sep. 23, 2004

(87) PCT Pub. No.: WO03/086072

PCT Pub. Date: Oct. 23, 2003

(65) Prior Publication Data

US 2005/0164156 A1 Jul. 28, 2005

(30) Foreign Application Priority Data

Mar. 28, 2002 (JP) ............................. 2002-091830

(51) Int. Cl.
*A01N 1/02* (2006.01)
*A61K 31/733* (2006.01)
*A61K 31/19* (2006.01)
*A61K 33/00* (2006.01)
*A61K 33/14* (2006.01)
*A61K 31/715* (2006.01)

(52) U.S. Cl. .................. 514/61; 424/601; 424/677; 424/678; 424/679; 424/680; 424/681; 424/715; 424/717; 424/722; 435/1.1; 435/1.2; 514/60; 514/557

(58) Field of Classification Search ................. 424/601, 424/677, 678, 679, 680, 681, 715, 717, 722; 435/1.1, 1.2; 514/60, 61, 557
See application file for complete search history.

(56) References Cited

U.S. PATENT DOCUMENTS 4,879,283 A * 11/1989 Belzer et al. ................. 435/1.2
5,306,508 A * 4/1994 Kossovsky et al. .......... 424/493

FOREIGN PATENT DOCUMENTS

| JP | 5-38284 A | | 2/1993 |
|----|-----------|---|--------|
| JP | 05038284 A | * | 2/1993 |
| JP | 6-40801 A | | 1/1994 |
| JP | 06040801 A | * | 2/1994 |
| JP | 7-99965 A | | 4/1995 |
| JP | 07099965 A | * | 4/1995 |
| JP | 8-34701 A | | 2/1996 |
| JP | 08034701 A | * | 2/1996 |
| JP | 09255501 A | * | 9/1997 |

OTHER PUBLICATIONS

Wang et al., Cryobiology, 1991, 28(2), 171-176.*
Miguel Bussiere, Jean E. Vance, Robert B. Campenot, and Dennis E. Vance, "Compartmentalization of Choline and Acetylcholine Metabolism in Cultured Sympathetic Neurons", Journal of Biochemistry, 2001, 130(4): 561-568.*
K. R. Niness, "Inulin and Oligofructose: What are They?", The Journal of Nutrition, 1999, 129, 1402S-1406S.*

* cited by examiner

*Primary Examiner*—John Pak
*Assistant Examiner*—Nathan W Schlientz
(74) *Attorney, Agent, or Firm*—Wenderoth, Lind & Ponack, L.L.P.

(57) ABSTRACT

The present invention relates to a composition for organ preservation, comprising an inulin type fructan as an active ingredient. The composition for organ preservation can suppress the hypofunction of an organ and damage to a histological structure and can improve the state of preservation of the organ in the course of organ transplantation and the like.

7 Claims, 6 Drawing Sheets

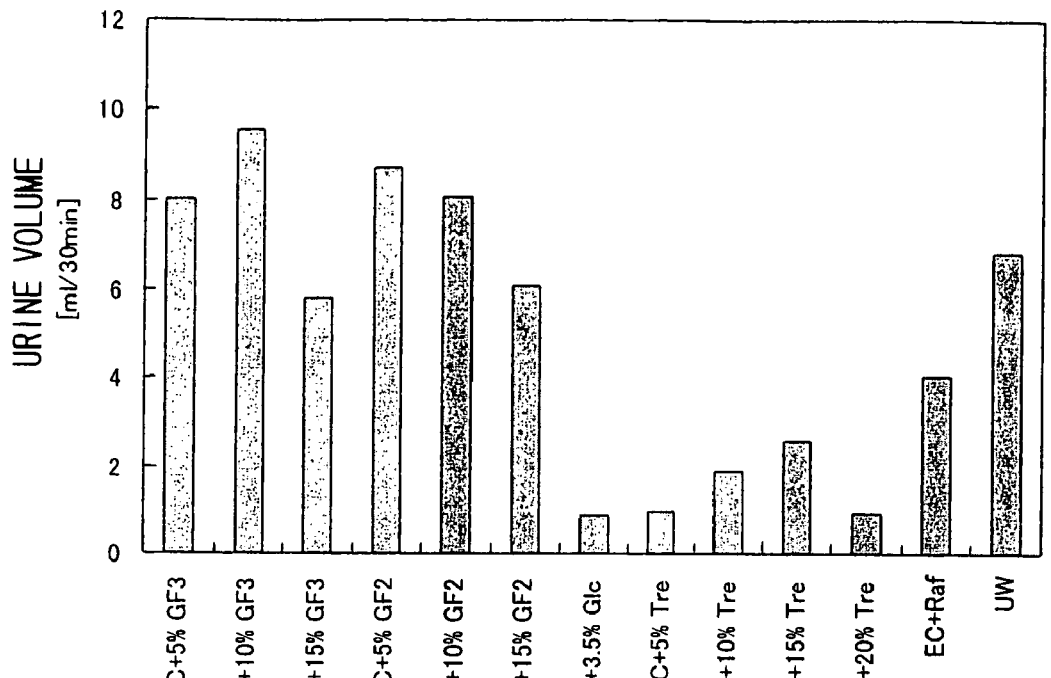
F I G. 1
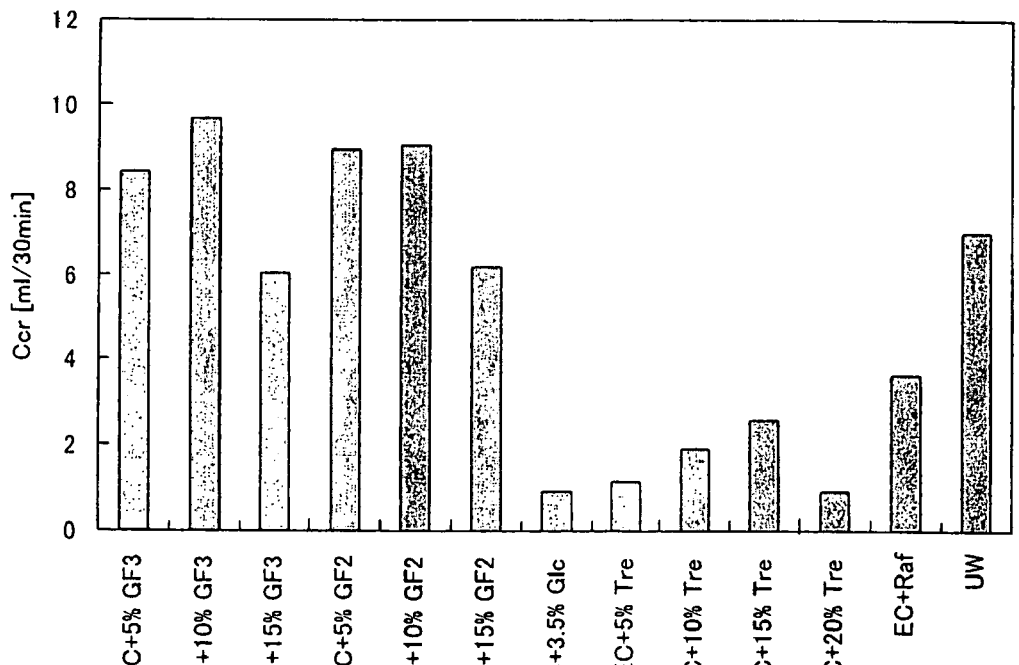
F I G. 2

COMPOSITION AND METHOD FOR ORGAN PRESERVATION

This application is a national stage of PCT/JP03/04024 filed Mar. 28, 2003. The entire contents of the above-identified application are hereby incorporated by reference. This application claims priority to JP 2002-91830 filed Mar. 28, 2002, the entirety of which is hereby incorporated by reference.

BACKGROUND OF THE INVENTION

1. Field of the Invention

The present invention relates to a composition for organ preservation comprising an inulin type fructan and a method for preserving an organ using the same.

2. Related Art

Organ transplantation can be adopted as last therapy in the case where commonly used therapy cannot be effectively carried out without difficulties because of severe organ diseases such as end-stage organ failure.

For example, in Japan, "The Law on Organ Transplantation (the so-called the Organ Transplant Law)" was enforced on October, 1997, and, in addition to conventionally approved organ transplantation from a living donor (particularly liver transplantation from a living donor), organ transplantation from a brain death donor has become legally possible. On the other hand, in Europe and United States, an organ donation system was already established at least 30 years ago, and up to now, there are not less than 40,000 cases for heart transplant and several hundreds of thousands of cases for kidney transplant. In Europe and United States, medical transplantation has become ubiquitous in society as a form of medical treatment.

The reason why transplantation therapy has become considered as one of safe therapies is that necessary environment is being in place, that is, for example, transplants can be satisfactorily secured, organ preservation techniques have been improved, transplantation techniques have been improved, and the control of rejection is possible. What is important in organ transplantation is not only to successfully enucleate an organ from a donor (an organ donor) and to successfully transplant the organ into a recipient (a donor recipient), but also to preserve the organ harvested from the donor in a good state. In general, when blood flow in organs in a living body is stopped for a long period of time, they are necrotized. For example, it is said that, when the liver is in an ischemic state for 30 to 90 min at room temperature, an irreversible change occurs. In the case of organ transplantation from a living donor, the amount of time between the enucleation of the organ and the transplantation can be regulated. On the other hand, in the case of organ transplantation from a brain death donor in which facilities where organ transplantation is carried out are different from facilities where the organ is harvested, there is a limitation on a reduction in the amount of time between the enucleation of the organ and the transplantation of the organ, because a lot of time is often taken for the selection of a recipient due to histocompatibility and the like and the transport of the organ and the like. One of important points, which have a decisive influence on whether or not organ transplantation can be conducted with successful results, is to preserve the harvested organ for the longest possible period of time while maintaining the structure and function of the organ.

The harvested organ is generally preserved by a low-temperature immersion method. In this method, initial perfusion (flushing) in which the harvested organ is washed with a cooled perfusate is conducted, and the organ is then subjected to low-temperature immersion preservation using a cooled preserving solution. The oxygen consumption can be suppressed by cooling the organ. When the organ is preserved in a cooled state, however, a sodium pump of cell membrane is broken. For this reason, the use, as a solution for organ preservation, of a solution having the same composition as a high-potassium/low-sodium intracellular fluid has been regarded as advantageous.

At first, for example, Collins solution containing glucose and an intracellular fluid-type electrolyte, and Euro-collins solution having the same composition as the Collins solution except for the absence of magnesium were used as the organ preservative. These preserving solutions are effective for the kidney, but on the other hand, the effect of protecting tissues and cells in organs other than the kidney is sometimes unsatisfactory.

In recent years, UW (University of Wisconsin) solution developed by a research group in University of Wisconsin has in many cases become used as an organ preservative. This UW solution can prolong preservation time of the liver and the pancreas and is disclosed, for example, in Japanese Patent Publication No. 68082/1995 (U.S. Pat. No. 4,879,283, German Patent No. 3843958) and Japanese Patent Publication No. 22801/1996. The UW solution is an electrolytic solution containing lactobionate and raffinose as an impermeation agent, hydroxyethyl starch as a colloid osmo-regulator, and adenosine or insulin as an energy metabolism promoting component. The is UW solution is commercially available from DuPont Pharmaceuticals under the tradename designation ViaSpan and is extensively used clinically. The UW solution, however, suffers from problems of stability and preparation methods. Further, since the UW solution is a preserving solution in a single commodity form, in some cases, it cannot be said that the UW solution can satisfactorily cope with various organs such as heart, liver, kidney, lung, pancreas, and small intestine.

Thus, there remains a need for an organ preservative which can alleviate the problem posed by the preservation of the organ, can improve the state of preservation of the organ, and can prolong the preservation time.

The organ preservative generally contains sugars such as glucose, raffinose, and mannitol. So far as the present inventors know, however, there is substantially no finding on what type of sugars is proper for organ preservation.

For example, Japanese Patent Laid-Open Publication No. 40801/1994 (Europe Patent Publication No. 0580444) discloses an organ preservative comprising trehalose, hydroxyethyl starch, and various electrolytes. This publication, however, does not disclose the applicability of inulin type fructans.

SUMMARY OF THE INVENTION

The present inventors have now found that, in preserving an organ, the use of an organ preservative containing an inulin type fructan can significantly suppress hypofunction of the preserved organ and damage to the histological structure of the preserved organ, whereby the state of preservation of the organ can be significantly improved. The present invention has been made based on such finding.

Accordingly, an object of the present invention is to provide a composition for organ preservation which has an excellent capability of maintaining the function and histological structure of an organ preserved.

According to the present invention, there is provided a composition for organ preservation, comprising an inulin type fructan as an active ingredient.

According to the present invention, there is also provided a method for preserving an organ, comprising the step of bringing an effective amount for organ preservation of the above composition for organ preservation into contact with an organ.

According to another aspect of the present invention, there is provided a method for suppressing or improving hypofunction of and damage to an organ which possibly occur during an organ transplantation process, said method comprising the step of bringing an effective amount for suppression or improvement of the above composition for organ preservation into contact with an organ.

According to the present invention, there is also provided use of an inulin type fructan for the manufacture of an organ preservative.

As compared with conventional organ preservatives, the composition for organ preservation according to the present invention can significantly suppress hypofunctioin of organs and damage to histological structure and can improve the state of preservation of the organs. Therefore, the composition for organ preservation and the method for preserving an organ according to the present invention can be extensively used in medical and clinical fields where transplantation organs are handled, as well as in various fields where the preservation of organs and the like is often necessary.

BRIEF DESCRIPTION OF THE DRAWINGS

FIG. 1 is a graph showing urine volume discharged from a kidney at the time when continuous perfusion was carried out for 60 min in an isolated perfusion kidney model in Example 1;

FIG. 2 is a graph showing creatinine clearance (Ccr) of a kidney at the time when continuous perfusion was carried out for 60 min in an isolated perfusion kidney model in Example 1;

FIGS. 3A and 3B are photographs of histological images (at a magnification of 100 times) of a kidney preserved using predetermined compositions for organ preservation at 4° C. for 48 hr in Example 1, wherein FIG. 3A shows a histological image in the case where composition 2 for organ preservation (EC+10% $GF_3$) was used, and FIG. 3B shows a histological image in the case where composition 13 for organ preservation (UW solution) was used;

FIGS. 4A and 4B are photographs of histological images (at a magnification of 100 times) of a liver preserved using predetermined compositions for organ preservation at 4° C. for 48 hr in Example 2, wherein FIG. 4A shows a histological image in the case where composition 1 for organ preservation (EC+5% $GF_3$) was used, and FIG. 4B shows a histological image in the case where composition 13 for organ preservation (UW solution) was used;

FIGS. 5A and 5B are photographs of histological images (at a magnification of 100 times) of a heart preserved using predetermined compositions for organ preservation at 4° C. for 24 hr in Example 3, wherein FIG. 5A shows a histological image in the case where composition 14 for organ preservation (EC+2.5% $GF_3$) was used, and FIG. 5B shows a histological image in the case where composition 15 for organ preservation (EC solution) was used; and FIGS. 6A and 6B are photographs of histological images (at a magnification of 100 times) of a lung preserved using predetermined compositions for organ preservation at 4° C. for 24 hr in Example 3, wherein FIG. 6A shows a histological image in the case where composition 14 for organ preservation (EC+2.5% $GF_3$) was used, and FIG. 6B shows a histological image in the case where composition 15 for organ preservation (EC solution) was used.

DETAILED DESCRIPTION OF THE INVENTION

Composition for Organ Preservation

Figure 3A:
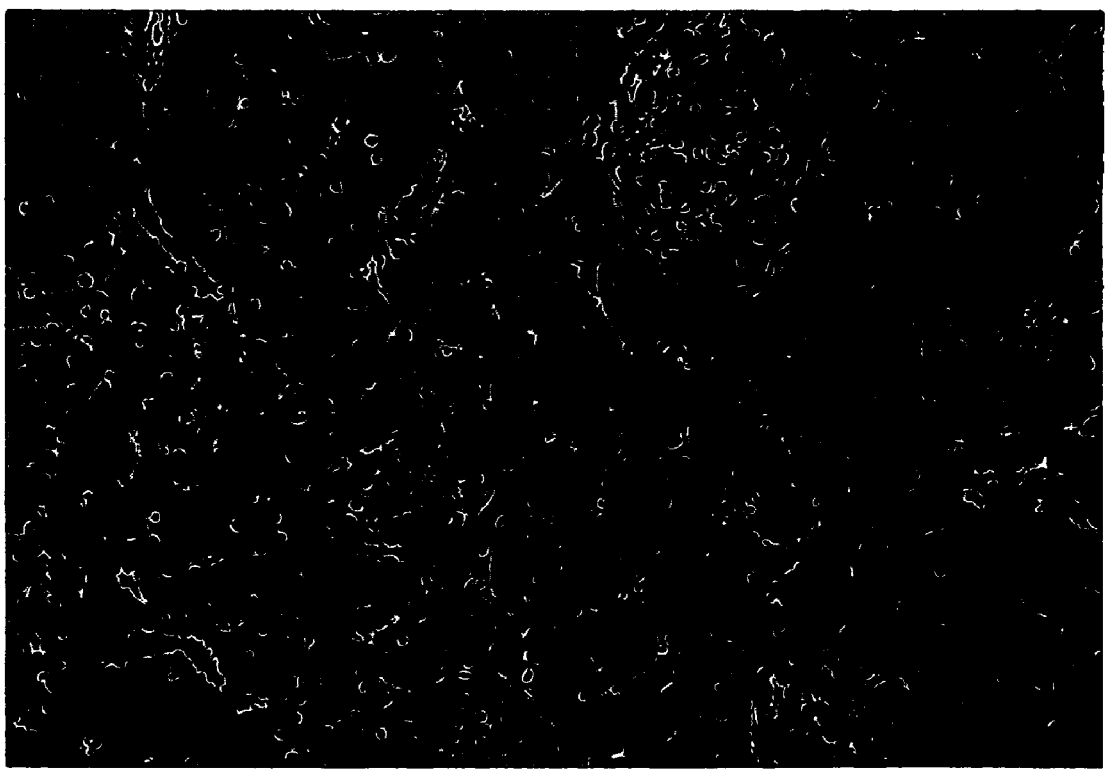

As described above, the composition for organ preservation according to the present invention comprises as an active ingredient an inulin type fructan.

The wording "comprises as an active ingredient" means that the composition may of course contain a carrier depending upon a desired dosage form and may also comprise other agents usable in combination with the active ingredient.

Inulin Type Fructan

Inulin type fructan is a fructan having a degree of polymerization of 3 or more in which fructose has been polymerized on sucrose through $\beta2\rightarrow1$ bond and glucose is bonded to the reducing end. Therefore, the inulin type fructan may be represented by a chemical structure $GF_n$ where G represents a glucosyl unit, F represents a fructosyl unit, and n represents the number of fructose molecules bonded to each other.

In the present invention, the degree of polymerization of the inulin type fructan is preferably 3 to 30, more preferably 3 to 6.

In the present invention, the inulin type fructan may be an inulin type fructan having a single degree of polymerization falling with the above-defined degree of polymerization range. Alternatively, the inulin type fructan may be a mixture of two or more inulin type fructans different from each other in degree of polymerization.

When the inulin type fructan is a mixture of two or more inulin type fructans different from each other in degree of polymerization, the ratio between these two or more inulin type fructans different from each other in degree of polymerization in the mixture may be any value. Preferably, however, the mixture is such that the proportion of the inulin type fructan having a degree of polymerization of 3 to 6 is not less than 10% by weight, more preferably not less than 55% by weight, still more preferably not less than 95% by weight.

In one preferred embodiment of the present invention, the inulin type fructan is a mixture of two or more inulin type fructans selected from inulin type fructans having a degree of polymerization of 3 to 6.

In another preferred embodiment of the present invention, the inulin type fructan is an inulin type fructan having a degree of polymerization of 3, that is, 1-kestose ($GF_2$).

In still another preferred embodiment of the present invention, the inulin type fructan is an inulin type fructan having a degree of polymerization of 4, that is, nystose ($GF_3$).

In the present invention, either naturally occurring inulin type fructan or chemically synthesized inulin type fructans may be used as the inulin type fructan.

The inulin type fructan is contained in roots and rhizomes of Iridaceae, Compositae, Liliaceae, Orchidaceae and other plants or in Gramineae grains. Therefore, the inulin type fructan can be obtained, for example, from chicory or Jerusalem Artichoke by extraction and/or purification according to a conventional method. The inulin type fructan may also be produced by allowing an enzyme having fructose transfer activity to act on sucrose. Further, an inulin type fructan having a desired degree of polymerization can be produced by allowing an enzyme, such as inulinase, inulin fructotransferase, or saccharase, to act on a high-molecular weight inulin type fructan. When the production of an inulin type fructan by synthesis is contemplated, the inulin type fructan may be synthesized by a conventional method.

Specific examples of inulin type fructans usable in the present invention will be described. Any of inulin type fructans and inulin type fructan mixtures obtained in the following process may be used in the present invention.

An inulin type fructan mixture containing not less than 55% by weight of inulin type fructans having a degree of polymerization of 3 to 6 (tradename: Meioligo G) (manufactured by Meiji Seika Kaisha Co., Ltd.) can be produced by allowing an enzyme derived from Aspergillus niger to act on sucrose. Purification of this inulin type fructan mixture, for example, by column chromatography or membrane separation can provide an inulin type fructan mixture of which the content of inulin type fructans having a degree of polymerization of 3 to 6 is higher. For example, an inulin type fructan product of is which the content of inulin type fructans having a degree of polymerization of 3 to 6 is not less than 95% by weight (tradename: Meioligo P) (manufactured by Meiji Seika Kaisha Co., Ltd.) can be obtained by purifying the above Meioligo G by column chromatography. Further purification by column 20 chromatography, crystallization or the like can provide an inulin type fructan composed mainly of a single component of, for example, 1-kestose (degree of polymerization: 3), nystose (degree of polymerization: 4), or fructosylnystose (degree of polymerization: 5).

The inulin type fructan naturally occurs and has human's dietary experiences and thus has no safety problem. When the inulin type fructan is used in the present invention, however, pyrogens which are often present as a mixture are preferably removed by a conventional method.

In the composition for organ preservation according to the present invention, the mixing amount of the inulin type fructan is not particularly limited and may be properly varied depending upon the type of usage and service condition of the composition. Therefore, for example, the composition may consist of the inulin type fructan alone. Further, for example, when the composition for organ preservation is used as a solvent, the content of the inulin type fructan in the solution of the composition for organ preservation is preferably 3.5 to 300 g/L, more preferably 50 to 150 g/L, most preferably 50 to 100 g/L. The concentration of the inulin type fructan may properly vary depending upon the organ to be preserved or perfused.

Optional Components

The composition for organ preservation according to the present invention may further comprise optional components in addition to the inulin type fructan. Examples of such optional components include sugars, electrolytes, organic acids, vitamins, amino acids, hormones, antibiotics, active oxygen scavengers, anticoagulants, antihypertensive agents, cryoprotective compounds, fibrinolytic agents, additives (carriers) for pharmaceutical preparations, and solvents.

Sugars include, for example, glucose, sucrose, lactose, raffinose, trehalose, stachyose, galactosyltrehalose, mannitol, sorbitol, maltitol, erythritol, palatinose, lactitol, xylitol, hydroxyethyl starch, and dextran.

Electrolytes include, for example, sodium chloride, potassium chloride, magnesium chloride, calcium chloride, sodium dihydrogenphosphate, potassium dihydrogenphosphate, disodium hydrogenphosphate, dipotassium hydrogenphosphate, sodium carbonate, and potassium carbonate.

Organic acids include, for example, gluconic acid, lactic acid, acetic acid, propionic acid, β-hydroxybutyrate, citric acid, fumaric acid, succinic acid, oxalic acid, and maleic acid.

In the present invention, when the composition for organ preservation has been dissolved in a predetermined solvent, or when the composition for organ preservation is in a solvent form, preferably, the solution containing the composition for organ preservation dissolved therein contains, in addition to the inulin type fructan, predetermined alkali metal ions, alkaline earth metal ions, and anions in a predetermined concentration. Therefore, when the above-described electrolyte, organic acid, or salt of the organic acid (for example, sodium salt or potassium salt) is incorporated in the composition for organ preservation according to the present invention, upon the dissolution of the composition for organ preservation, desired ions can be produced.

In a preferred embodiment of the present invention, when the composition for organ preservation is a liquid preparation, the composition for organ preservation comprises the following components (a) to (d) in the following respective amounts:

| | |
|---|---|
| (a) inulin type fructan | 3.5 to 300 g/L; |
| (b) Na$^+$ | 5 to 150 mM; |
| (c) K$^+$ and | 5 to 150 mM; |
| (d) at least one component selected from the group consisting of Cl$^-$, HCO$_3^-$, CO$_3^{2-}$, organic acids, and organic acid anions | 10 to 150 mM. |

The concentration of Na ions as component (b) is preferably 10 to 30 mM.

The concentration of K ions as component (c) is preferably 115 to 120 mM.

Component (d) is preferably Cl$^-$, HCO$_3^-$ and/or CO$_3^{2-}$. The concentration of component (d) is preferably 25 to 104 mM.

In a more preferred embodiment of the present invention, when the composition for organ preservation is a liquid preparation, the composition for organ preservation further comprises at least one of the following components (e) to (h) in the following respective amounts:

| | |
|---|---|
| (e) Mg$^{2+}$ | 0 to 20 mM; |
| (f) Ca$^{2+}$ | 0 to 5 mM; |
| (g) H$_2$PO$_4^-$ and/or HPO$_4^{2-}$ and | 0 to 150 mM; |
| (h) hydroxyethyl starch | 0 to 100 g/L. |

The concentration of Mg ions as component (e) is preferably 0 to 5 mM.

The concentration of Ca ions as component (f) is preferably 0 to 5 mM.

Component (g) is preferably H$_2$PO$_4^-$ and HPO$_4^{2-}$. The concentration of component (g) is preferably 25 to 57.5 mM.

The concentration of the hydroxyethyl starch as component (h) is preferably 0 to 50 g/L.

In a still more preferred embodiment of the present invention, when the composition for organ preservation is a liquid preparation, the composition for organ preservation comprises the following components (a') to (h') in the following respective amounts:

| | |
|---|---|
| (a') inulin type fructan | 50 to 150 g/L; |
| (b') Na$^+$ | 10 to 30 mM; |
| (c') K$^+$ | 115 to 120 mM; |
| (d') at least one component selected | 25 to 104 mM; |

-continued

| | |
|---|---|
| from the group consisting of $Cl^-$, $HCO_3^-$, $CO_3^{2-}$, organic acids, and organic acid anions | |
| (e') $Mg^{++}$ | 0 to 5 mM; |
| (g') $H_2PO_4^-$ and $HPO_4^{2-}$ and | 25 to 57.5 mM; |
| (h') hydroxyethyl starch | 0 to 50 g/L. |

A specific example of the composition for organ preservation according to the present invention comprises the following components (a') to (h') in the following respective amounts:

| | |
|---|---|
| inulin type fructan | 50 to 100 g/L |
| $Na^+$ | 10 mM |
| $K^+$ | 115 mM |
| $Cl^-$ | 15 mM |
| $HCO_3^-$ | 10 mM |
| $H_2PO_4^-$ | 15 mM |
| $HPO_4^{2-}$ | 42.5 mM. |

In the present invention, regarding ion composition other than the inulin type fructan, the composition may be prepared by changing or omitting a part of the components constituting a conventional solution for organ preservation, for example, Euro-Collins solution, UW (University of Wisconsin) solution, or Celsior solution. For example, the composition for organ preservation according to the present invention may be prepared by substituting the inulin type fructan for the whole or a part of sugars such as glucose or raffinose in the components constituting a conventional solution for organ preservation.

Regarding the above optional components, hormones include, for example, dexamesone and hydrocortisone, and antibiotics include, for example, penicillin G and streptomycin. Anticoagulants include, for example, heparin, antihypertensive agents include, for example, vasodilators and chlorpromazine, and thrombolytic agents include, for example, urokinase.

Additives for pharmaceutical preparations include, for example, vehicles, dispersants, preservatives, antiseptics, emulsifiers, extenders, colorants, surfactants, buffers, solubilizers, stabilizers, and pH adjustors.

Solvents include, for example, purified water, sterilized pure water, and physiological saline.

Production Process and Use of Composition for Organ Preservation

The composition for organ preservation according to the present invention can easily be produced by a person having ordinary skill in the art in the same manner as used in the production of a conventional organ preservative, except that an inulin type fructan is used.

The dosage form of the composition for organ preservation according to the present invention is usually a liquid preparation containing the above solvent. If necessary, the dosage form of the composition for organ preservation according to the present invention may be solid preparations such as powders, granules, tablets, and capsules. In the case of the solid preparation, in use, the solid preparation can be dissolved, suspended, or emulsified in a suitable solvent such as purified water, sterilized pure water, and physiological saline.

In the present invention, the organ preservation includes, of course, temporary preservation of an organ enucleated in the course of organ transplantation and further embraces perfusion of an organ in the course of organ transplantation and protection of an organ not in an enucleated state or an organ after transplantation against various diseases or damage.

The composition for organ preservation according to the present invention can be used in the preservation and perfusion of an organ. For example, the composition for organ preservation according to the present invention may be used as a preserving solution for an organ and a perfusate for an organ. The composition for organ preservation according to the present invention is preferably used for suppression or improvement of hypofunction of and damage to an organ which possibly occur in the course of organ transplantation.

In the present invention, organs are not limited to organs in a narrow sense such as heart, liver, kidney, lung, and pancreas and include such tissues as intestinal tracts, blood, bone marrow, eyeball, cornea, bone, skin, blood vessel, and heart valve.

Accordingly, the composition for organ preservation according to the present invention is suitable for use in preservation of these organs. Preferably, the composition for organ preservation according to the present invention is used for heart, liver, kidney, lung, and pancreas, more preferably for heart, liver, kidney, and lung, more preferably for kidney.

According to the present invention, there is provided a method for preserving an organ, comprising the step of bringing an effective amount for organ preservation of the above composition for organ preservation into contact with an organ.

The effective amount for organ preservation refers to an amount necessary for effectively preserving an organ and may be properly determined depending upon the type and state of the organ, the form of the composition for organ preservation and the like.

Further, the wording "bringing the composition for organ preservation into contact with an organ" means that at least the composition for organ preservation and the organ may be brought into contact with each other by any embodiment which includes, for example, application of the composition for organ preservation onto the organ, immersion of the organ in a solution comprising the composition for organ preservation, and perfusion of the organ with the composition for organ preservation. When the organ is immersed in the solution, preferably, the immersion is carried out under low temperature conditions.

In a preferred embodiment of the present invention, there is provided a method for preserving an organ, comprising the step of bringing an effective amount for organ preservation of the above composition for organ preservation into contact with an organ, the organ is immersed in the composition for is organ preservation in a cooled solvent form at a low temperature. More preferably, the preservation method further comprises, before the step of immersing the organ, the step of perfusing an enucleated organ using the composition for organ preservation in a cooled solvent form as a perfusate. The term "low temperature" as used herein refers to 0 to 4° C., preferably 3 to 4° C., and a specific example of the low temperature is about 4° C. The amount of the composition for organ preservation in a solvent form used in the preservation of an organ may be properly varied depending, for example, upon the weight and predetermined preservation time of the organ. In general, however, the amount of the composition is large enough to immerse the organ. For example, in the case of human kidney, the amount of the composition used may be 800 ml per about 400 g of the kidney.

According to another aspect of the present invention, there is provided a method for suppressing or improving hypofunction of and damage to an organ which possibly occur during an organ transplantation process, said method comprising the step of bringing an effective amount for suppression or improvement of the above composition for organ preservation into contact with an organ.

The effective amount for suppression or improvement refers to an amount necessary for effectively suppressing or improving hypofunction of and damage to the organ and may properly be determined depending upon the type and state of the organ, the form of the composition for organ preservation and the like.

Examples of the "hypofunction of and damage to an organ which possibly occur during an organ transplantation process" include symptoms such as edematization of cells involved in Na/K pump disorder, disorder of cell membrane and mitochondria due to a rise in Ca concentration, and production of hypoxanthine from ATP.

Further, according to the present invention, there is provided use of an inulin type fructan for the manufacture of a composition for organ preservation or an organ preservative. The organ preservative refers to a pharmaceutical for use in the preservation of an organ and may comprise the composition for organ preservation according to the present invention. The composition for organ preservation or the organ preservative may be in the form of a preserving solution or a perfusate.

EXAMPLES

The present invention is further illustrated by the following Examples that are not intended as a limitation of the invention.

Example 1

Preservation Test of Kidney (a) Preparation of Composition for Organ Preservation Compositions 1 to 6 for organ preservation according to the present invention and compositions 7 to 13 for organ preservation as comparative examples were prepared as follows.

Compositions 1 to 3 for Organ Preservation (Present Invention)

In 465 ml of a commercially available Euro-collins solution (EC solution, manufactured by Yoshitomi Pharmaceutical Industries, Ltd.) were dissolved 25 g, 50 g, and 75 g of Nystose (manufactured by Meiji Seika Kaisha Co., Ltd.) to prepare compositions 1 to 3 for organ preservation. These compositions 1 to 3 will be hereinafter often referred to as EC+5% $GF_3$, EC+10% $GF_3$, and EC+15% $GF_3$, respectively.

The EC solution used was a solution not containing a glucose injection and had the electrolyte composition as follows.

| | | |
|---|---|---|
| | $Na^+$ | 10 mM |
| | $K^+$ | 115 mM |
| | $Cl^-$ | 15 mM |
| | $HCO_3^-$ | 10 mM |
| | $H_2PO_4^-$ | 15 mM |
| | $HPO_4^{2-}$ | 42.5 mM. |

Compositions 4 to 6 for Organ Preservation (Present Invention)

In 465 ml of the same EC solution as in composition 1 for organ preservation were dissolved 25 g, 50 g, and 75 g of 1-kestose (manufactured by Meiji Seika Kaisha Co., Ltd.) to prepare compositions 4 to 6 for organ preservation. These compositions 4 to 6 will be hereinafter often referred to as EC+5% $GF_2$, EC+10% $GF_2$, and EC+15% $GF_2$, respectively.

Composition 7 for Organ Preservation (Comparative Example)

A Japanese Pharmacopeia glucose injection (50% w/v) (35 ml) was added to 465 ml of the same EC solution as in composition 1 for organ preservation to bring the total volume of the solution to 500 ml to prepare composition 7 for organ preservation. This composition 7 will be hereinafter often referred to as EC+3.5% Glc.

Compositions 8 to 11 for Organ Preservation (Comparative Examples)

In 465 ml of the same EC solution as in composition 1 for organ preservation were dissolved 25 g, 50 g, 75 g, and 100 g of trehalose (manufactured by Hayashibara Co., Ltd.) to prepare compositions 8 to 11 for organ preservation. These compositions 8 to 11 will be hereinafter often referred to as EC+5% Tre, EC+10% Tre, EC+15% Tre, and EC+20% Tre, respectively.

Composition 12 for Organ Preservation (Comparative Example)

Raffinose (manufactured by Nippon Beet Sugar Manufacturing Co., Ltd.) was dissolved in the same EC solution as in composition 1 for organ preservation to bring the osmotic pressure to 320 mOsm/kg to prepare composition 12 for organ preservation. This composition 12 will be hereinafter often referred to as EC+Raf.

Composition 13 for Organ Preservation (Comparative Example)

A commercially available UW solution (tradename: Viaspan, manufactured by DuPont Pharmaceuticals) was used as composition 13 for organ preservation.

(b) Evaluation Test: Evaluation of Kidney Function Using Isolated Perfusion Kidney Model Nembutal (50 mg/kg) (tradename; manufactured by Dainabot Co., Ltd.) was intraperitoneally administered to SD rats (about 400 g) (available from Japan SLC Inc.) for anesthetization of the rats. Subsequently, 1 ml of heparin was administered to the rats, and the kidney was then perfused with the composition for organ preservation cooled to 4° C. Thereafter, the kidney was enucleated from the rats. The enucleated kidney was immediately transferred to the composition for organ preservation cooled to 4° C. and, in this state, was preserved at 4° C. for 48 hr. After the preservation for 48 hr, the kidney was subjected to continuous perfusion in a TN type enucleated organ perfusion apparatus (manufactured by Natsume Seisakusho Co., Ltd.) with a Krebs-Henseleit solution containing 7.5% bovine albumin as a perfusate for 90 min.

Urine Volume and Creatinine Clearance

At the end of perfusion for 30 min, 60 min, and 90 min, urine volume and creatinine clearance (Ccr) were measured.

For the urine volume, a polyethylene tube was inserted into the ureter, and the volume of urine discharged in a predetermined period of time was measured. Ccr was calculated based on equation (1).

Ccr=(creatinine value in urine)×(urine volume per predetermined period of time)/(creatinine value in perfusate)     (1)

The results were as shown in Table 1 and FIGS. 1 and 2.

In Table 1, the results were expressed in terms of average values and standard deviations for measured data obtained using the kidney of 8 rats for each composition. In FIGS. 1 and 2, the urine volume and Ccr at the end of perfusion for 60 min are shown.

In these results, for both the urine volume value and the Ccr value, the higher the value, the better preservation of kidney function. That is, in this case, the state of preservation of the kidney is good.

In the case of the preservation of the kidney using compositions 1, 2, 4 and 5 for organ preservation, both the urine volume value and the Ccr value were significantly higher than the values in the case where comparative compositions for organ preservation.

Observation of Histological Image

The kidney after preservation in the composition for organ preservation for 48 hr was evaluated for the state of preservation based on histological observation.

The histological image of the kidney preserved using composition 2 for organ preservation (EC+10% $GF_3$) was as shown in FIG. 3A.

For the kidney in this case, tubular epithelial cells and brush border were well preserved, glomeruli remained unchanged.

For the kidney preserved using composition 4 for organ preservation (EC+5% $GF_2$), the brush border was partly degenerated and fallen off. However, tubular epithelial cells were well preserved. Further, glomeruli remained unchanged, and the state of preservation was good.

For the kidney preserved using composition 7 for organ preservation (EC+3.5% Glc), glomeruli remained unchanged. However, swelling and vacuolar degeneration were observed in proximal convoluted tubular epithelial cells.

For the kidney preserved using composition 12 for organ preservation (EC+Raf), many nucleus components were observed on the outer side of sites which appeared to be vascular pole of glomeruli, and infiltration of inflammatory cells was also suggested. Further, falling-off of tubular epithelial cells was slightly observed.

Figure 3B:
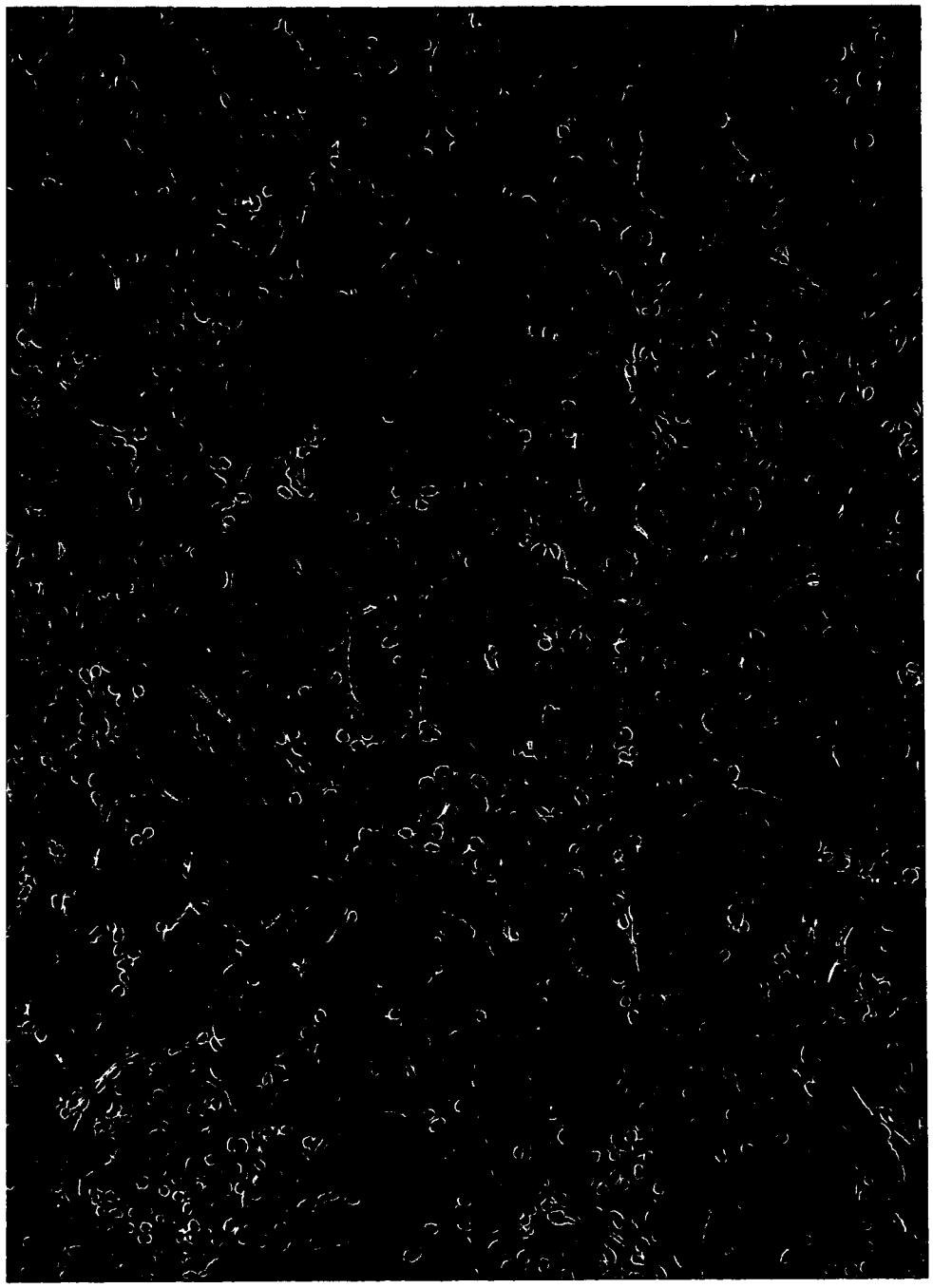

A histological image of the kidney preserved using composition 13 for organ preservation (UW solution) was as shown in FIG. 3B. For the kidney in this case, glomeruli were well preserved. However, falling-off and vacuolar degeneration of proximal convoluted tubular epithelial cells were slightly observed on the outer side of the cortex.

TABLE 1

| Composition for organ preservation | | Perfusion time (min) | Urine volume (ml/30 min) | Ccr (ml/30 min) |
|---|---|---|---|---|
| No. | Composition | | | |
| 1 | EC + 5% $GF_3$ | 30 | 5.58 ± 1.91 | 6.11 ± 2.34 |
| | | 60 | 8.05 ± 1.85 | 8.40 ± 2.13 |
| | | 90 | 6.61 ± 2.21 | 6.72 ± 2.20 |
| 2 | EC + 10% $GF_3$ | 30 | 5.32 ± 1.95 | 5.51 ± 2.13 |
| | | 60 | 9.54 ± 3.38 | 9.66 ± 3.57 |
| | | 90 | 8.96 ± 4.63 | 9.09 ± 4.81 |
| 3 | EC + 15% $GF_3$ | 30 | 3.26 ± 1.42 | 3.40 ± 1.53 |
| | | 60 | 5.83 ± 2.17 | 6.04 ± 2.31 |
| | | 90 | 5.63 ± 2.60 | 5.73 ± 2.51 |
| 4 | EC + 5% $GF_2$ | 30 | 3.26 ± 0.70 | 3.37 ± 0.82 |
| | | 60 | 8.73 ± 3.35 | 8.93 ± 3.35 |
| | | 90 | 8.93 ± 4.18 | 9.18 ± 4.43 |
| 5 | EC + 10% $GF_2$ | 30 | 3.90 ± 1.86 | 4.83 ± 1.37 |
| | | 60 | 8.07 ± 2.94 | 9.03 ± 2.34 |
| | | 90 | 8.32 ± 2.79 | 8.39 ± 2.81 |
| 6 | EC + 15% $GF_2$ | 30 | 2.68 ± 0.76 | 2.79 ± 0.77 |
| | | 60 | 6.11 ± 1.06 | 6.16 ± 1.11 |
| | | 90 | 5.54 ± 1.10 | 5.49 ± 1.11 |
| 7 (Comp. Ex.) | EC + 3.5% Glc | 30 | 0.26 ± 0.06 | 0.26 ± 0.06 |
| | | 60 | 0.86 ± 0.29 | 0.93 ± 0.33 |
| | | 90 | 1.21 ± 0.47 | 1.20 ± 0.45 |
| 8 (Comp. Ex.) | EC + 5% Tre | 30 | 0.73 ± 0.48 | 0.80 ± 0.53 |
| | | 60 | 0.99 ± 0.66 | 1.14 ± 0.68 |
| | | 90 | 0.92 ± 0.47 | 1.03 ± 0.45 |
| 9 (Comp. Ex.) | EC + 10% Tre | 30 | 1.35 ± 0.51 | 1.41 ± 0.56 |
| | | 60 | 1.89 ± 1.11 | 1.92 ± 1.16 |
| | | 90 | 2.16 ± 0.80 | 2.07 ± 0.70 |
| 10 (Comp. Ex.) | EC + 15% Tre | 30 | 1.38 ± 0.70 | 1.47 ± 0.67 |
| | | 60 | 2.58 ± 1.57 | 2.57 ± 1.44 |
| | | 90 | 2.85 ± 1.46 | 2.77 ± 1.31 |
| 11 (Comp. Ex.) | EC + 20% Tre | 30 | 0.46 ± 0.40 | 0.54 ± 0.41 |
| | | 60 | 0.93 ± 1.00 | 0.91 ± 0.92 |
| | | 90 | 0.78 ± 0.61 | 0.80 ± 0.60 |
| 12 (Comp. Ex.) | EC + Raf | 30 | 2.34 ± 1.20 | 2.29 ± 1.14 |
| | | 60 | 4.07 ± 2.06 | 3.64 ± 1.56 |
| | | 90 | 3.22 ± 2.28 | 3.01 ± 1.97 |
| 13 (Comp. Ex.) | UW solution | 30 | 3.53 ± 1.27 | 3.66 ± 1.34 |
| | | 60 | 6.82 ± 2.01 | 6.99 ± 1.97 |
| | | 90 | 6.68 ± 1.73 | 6.84 ± 1.86 |

Example 2

Preservation Test of Liver

In the same manner as in Example 1, composition 1 for organ preservation (EC+5% $GF_3$) and composition 13 for organ preservation (UW solution) were prepared. These compositions were used for the following tests.

Rats (around 400 g) were subjected to general anesthesia, and laparotomy was then performed. ELASTOR was inserted into a portal vein, and 5 ml of the composition for organ preservation cooled to 4° C. was allowed to flow into the vein. After whitening of the liver was confirmed, the artery in the upper part of the liver was clamped. Subsequently, the inferior vena cava was incised. Thereafter, 20 ml of the composition for organ preservation was allowed to flow into ELASTOR, and the liver was enucleated. The enucleated liver was simply cooled and preserved in the composition for organ preservation for 48 hr.

After the preservation for 48 hr, liver tissue was extracted and was fixed in 10% formalin. This liver tissue was evaluated for the state of preservation based on histological observation.

Figure 4A:
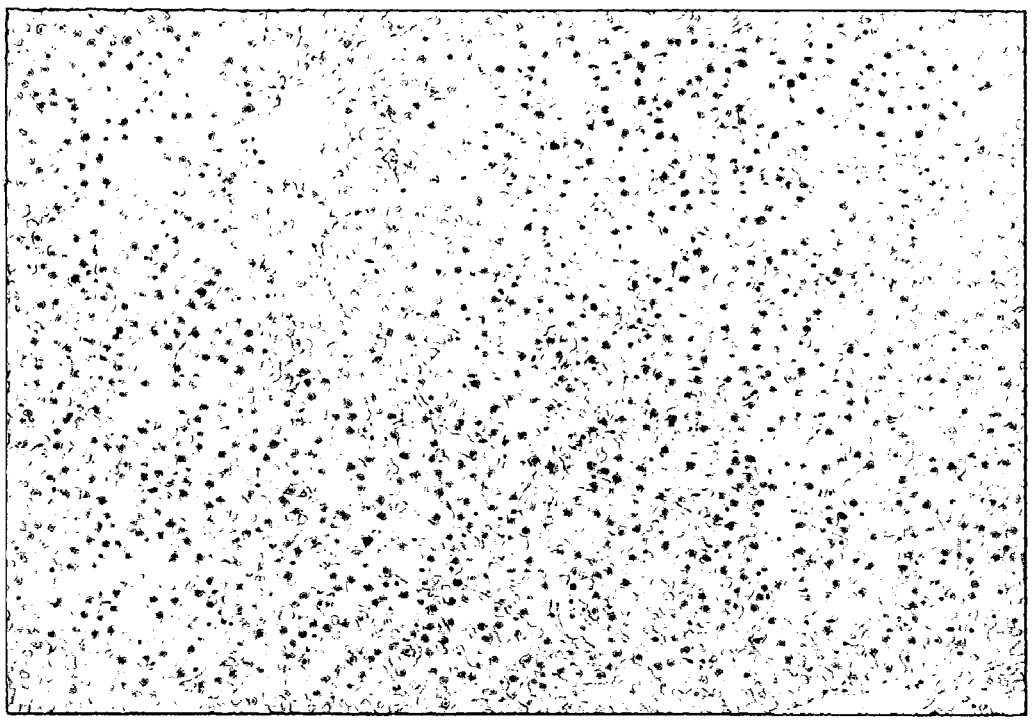
Figure 4B:
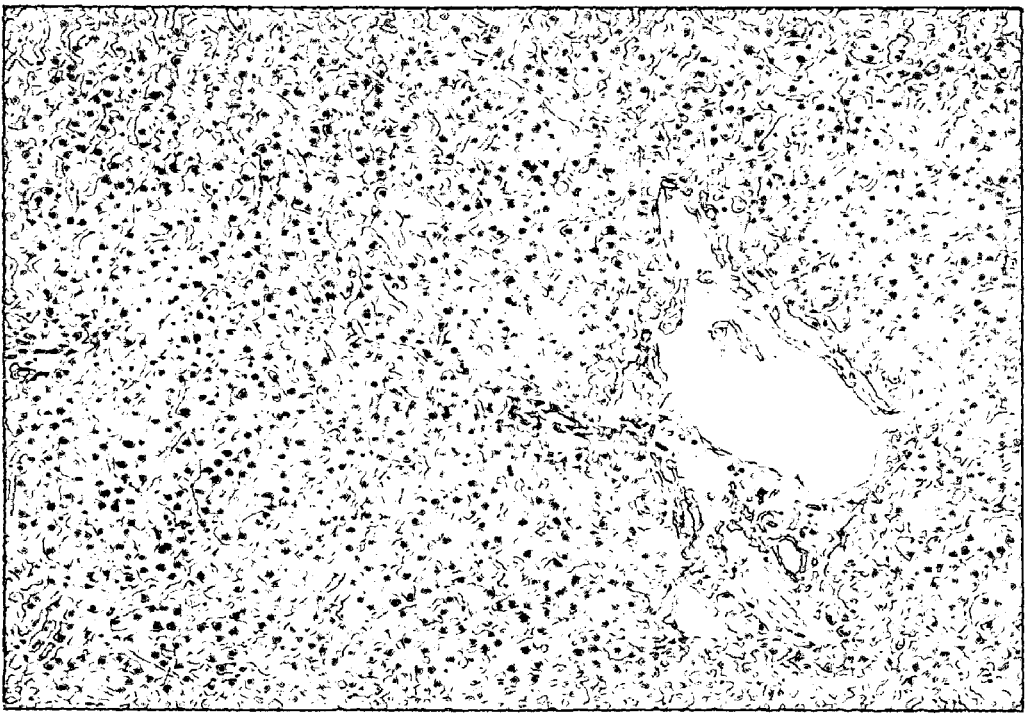

A histological image of the liver tissue was as shown in FIGS. 4A and 4B. FIG. 4A shows a histological image in the case where composition 1 for organ preservation (EC+5% $GF_3$) was used, and FIG. 4B shows a histological image in the case where composition 13 for organ preservation (UW solution) was used.

For the liver preserved using composition 1 for organ preservation, only mild atrophy of hepatocytes was observed, and the state of preservation was good. On the other hand, for the liver preserved using composition 13 for organ preservation, considerable atrophy was observed in hepatocytes, and a tendency toward hepatocyte dissociation was observed. Further, there was also mild to medium degeneration.

Example 3

Preservation Test of Heart and Lung

In the same manner as in Example 1, composition 14 for organ preservation (EC+2.5% $GF_3$) and composition 15 for organ preservation (EC solution alone) were prepared. These compositions were used for the following tests.

Rats (around 400 g) were subjected to general anesthesia, and laparotomy was then performed. The periphery of the inferior aorta was ligated. ELASTOR was inserted, and the survical vein and the inferior vena cava were incised. Thereafter, 60 ml of the composition for organ preservation was allowed to flow through the ELASTOR, and the heart and the lung were enucleated. The enucleated heart and lung were simply cooled and preserved in the composition for organ preservation for 24 hr.

After the preservation for 24 hr, a part of each of the organs was extracted and fixed in 10% formalin. The organs were evaluated for the state of preservation based on histological observation.

Figure 5A:
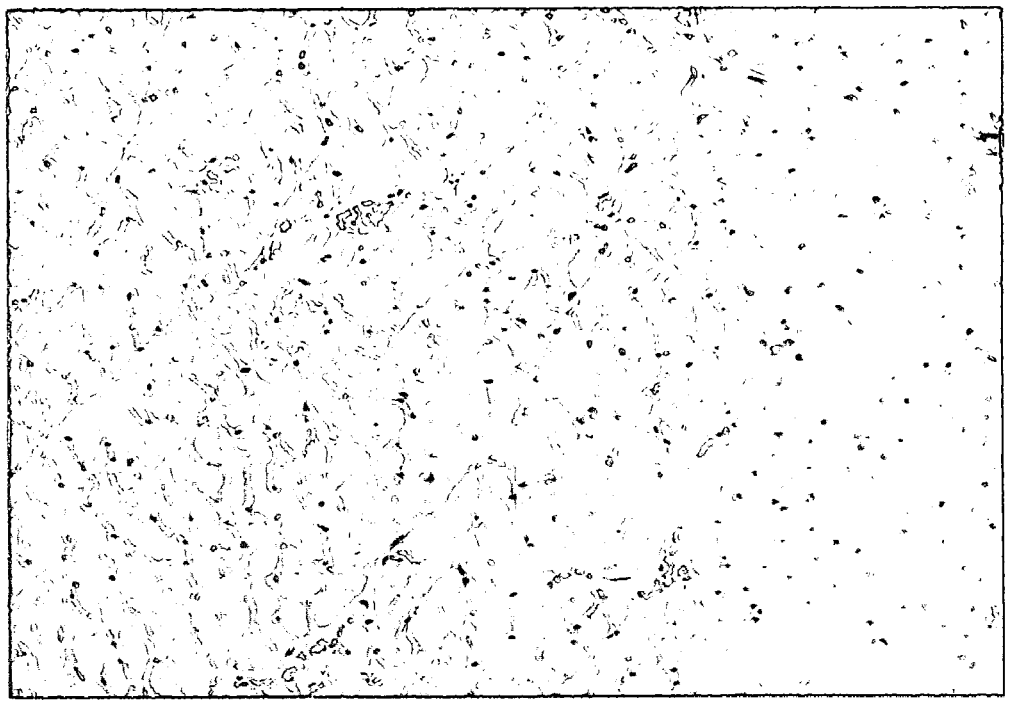
Figure 5B:
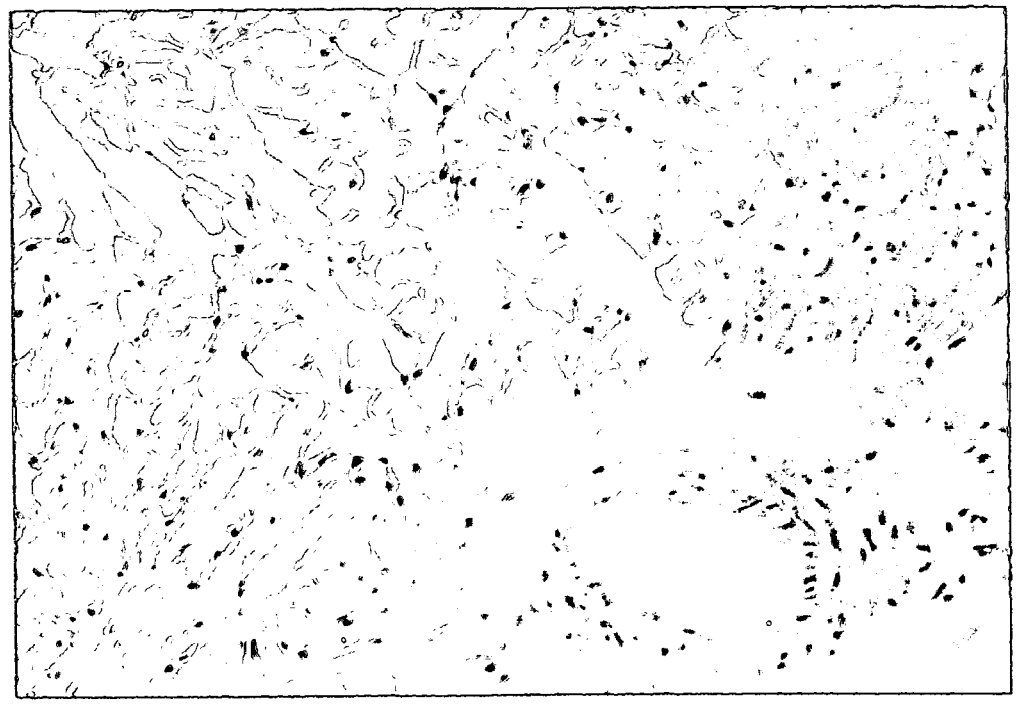
Figure 6A:
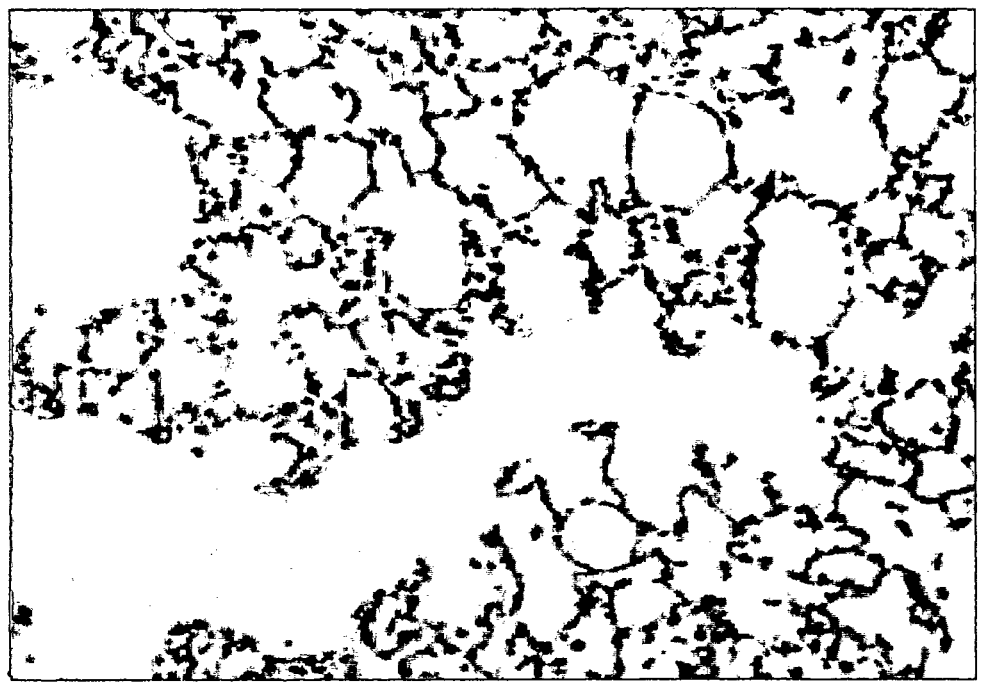
Figure 6B:
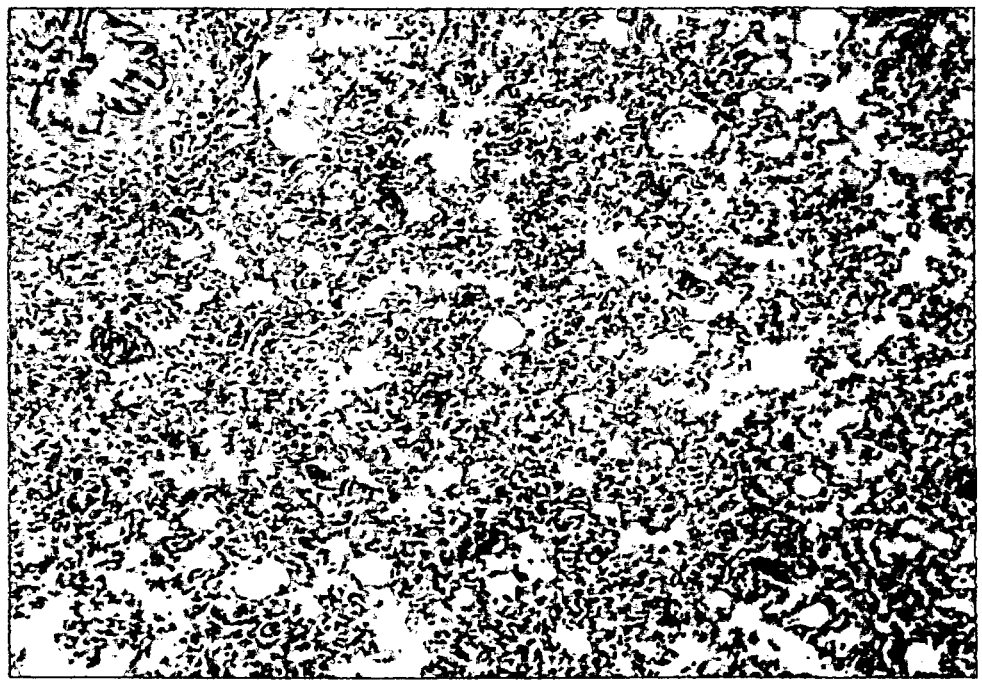

Histological images of the heart were as shown in FIGS. 5A and 5B, and histological images of the lung were as shown in FIGS. 6A and 6B. FIGS. 5A and 6A show histological images in the case where composition 14 for organ preservation (EC+2.50% GF₃) was used, and FIGS. 5B and 6B show histological images in the case where composition 15 for organ preservation (EC solution) was used.

For the heart preserved using composition 14 for organ preservation, neither an increase in acidophil nor pyknosis was observed, and the state of preservation was good. Further, for the lung preserved using composition 14 for organ preservation, the alveolar space was in a well opened state, and diapedesis was also not observed. Thus, the state of preservation was good.

On the other hand, for the heart preserved using composition 15 for organ preservation, an increase in acidophil of myoepicardial fibers was observed, and the nucleus was rendered lucent. Further, striation became partially unclear. For the lung preserved using composition 15 for organ preservation, the degeneration of elastic fibers of the walls of alveoli and the atrophy of alveoli were observed. Further, the degeneration of endothelial cells resulted in diapedesis.

The invention claimed is:

1. A composition for organ preservation, comprising an inulin type fructan as an active ingredient in an amount effective for preservation of the organ, wherein the composition comprises:

| (a) | inulin type fructan selected from the group consisting of 1-kestose, nystose, and a mixture thereof | 3.5-300 g/L; |
|---|---|---|
| (b) | Na⁺ | 5-150 mM; |
| (c) | K⁺ | 5-150 mM; |
| | at least one component selected from the group consisting of Cl⁻, HCO₃⁻, CO₃²⁻, organic acids, and organic acid anions | 10-150 mM. |

2. A composition for organ preservation, comprising an inulin type fructan as an active ingredient in an amount effective for preservation of the organ, wherein the composition comprises:

| (a) | inulin type fructan selected from the group consisting of 1-kestose, nystose, and a mixture thereof | 3.5-300 g/L; |
|---|---|---|
| (b) | Na⁺ | 5-150 mM; |
| (c) | K⁺ | 5-150 mM; |
| (d) | at least one component selected from the group consisting of Cl⁻, HCO₃⁻, CO₃²⁻, organic acids, and organic acid anions | 10-150 mM; |
| (e) | Mg²⁺ | 0-20 mM; |
| (f) | Ca²⁺ | 0-5 mM; |
| (g) | H₂PO₄⁻ and/or HPO₄²⁻ | 0-150 mM; and |
| (h) | hydroxyethyl starch | 0-100 g/L. |

3. A method for preserving an organ, comprising the step of bringing an effective amount for organ preservation of the composition for organ preservation according to claim 1 into contact with an organ.

4. The method according to claim 3, wherein said contact is carried out by perfusing the organ with the composition for organ preservation.

5. The method according to claim 3, wherein said organ is selected from the group consisting of kidney, liver, heart, lung, and pancreas.

6. The method according to claim 3, wherein said composition is cooled to 0 to 40° C. prior to said contact.

7. A method for suppressing hypofunction of and damage to an organ during an organ transplantation process, or improving hypofunction of an organ during an organ transplantation process, said method comprising the step of bringing an effective amount for suppression or improvement of the composition for organ preservation according to claim 1 into contact with an organ.

\* \* \* \* \*